United States Patent [19]

Bernstein

[11] 4,416,886

[45] Nov. 22, 1983

[54] METHOD OF TREATING PRURITIS AND COMPOSITION THEREFOR

[75] Inventor: Joel E. Bernstein, Deerfield, Ill.

[73] Assignee: Dermall Limited, Northbrook, Ill.

[21] Appl. No.: 288,166

[22] Filed: Jul. 29, 1981

[51] Int. Cl.³ .......................................... A61K 31/485
[52] U.S. Cl. ................................................... 424/260
[58] Field of Search ......................................... 424/260

[56] References Cited

U.S. PATENT DOCUMENTS 4,181,726  1/1980  Bernstein ............................. 424/260

OTHER PUBLICATIONS

Chem. Abstr., vol. 77, Entry 105601q, (1972).

Primary Examiner—Leonard Schenkman
Attorney, Agent, or Firm—Emrich & Lee and Brown, Hill, Dithmar, Stotland, Stratman & Levy

[57] ABSTRACT

A topical treatment for relieving pruritis wherein naloxone, a pharmaceutically acceptable salt or a pharmaceutically acceptable chemical derivative is topically applied in a lotion, solution, cream or ointment.

9 Claims, No Drawings

METHOD OF TREATING PRURITIS AND COMPOSITION THEREFOR

BACKGROUND OF THE INVENTION

Itching or pruritis is a common dermatologic symptom. The causes of pruritis are complex and poorly understood. The best understood mechanism of itching is the release of histamine in the skin leading to urticarial wheals and intense itching. Such itching has traditionally been relieved by antihistamines. While antihistamine therapy is often effective, the sedation and drowsiness produced by antihistaminic agents limits their effectiveness.

Many kinds of itching are not however easily relieved by antihistamines. For example, conditions such as Hodgkin's Disease, mycosis fungoides (cutaneous malignacy) and severe jaundice produce intense itching unrelieved by antihistamines. Therefore, there is a need for improved treatment to relieve severe itching which can not only be an alternative to antihistaminic treatment of itching due to such causes as mosquitoe bites which responds to such treatment, but which further provides relief in intractable cases of pruritis which heretofore have been virtually impossible to treat except as disclosed in my prior U.S. Pat. No. 4,181,726 issued Jan. 1, 1980, a method based on the systemic effect on the central nervous system. The present invention provides such a composition and method independent of systemic effects on the central nervous system.

Naloxone is a narcotic antagonist which is not known to cause physical or psychological dependence and which exhibits essentially no pharmacological activity in non-addicts. Naloxone is normally given by injection to addicts to assist them in narcotic withdrawal and sometimes is administered to post operative patients for partial reversal of narcotic depression following the use of narcotics during surgery.

It has been found surprisingly that topical applications of naloxone are useful in alleviating severe itching in various conditions.

SUMMARY OF THE INVENTION

The present invention provides an improved composition and method of treating severe itching comprising topically administering a therapeutically effective amount of naloxone or a pharmaceutically acceptable salt thereof or a pharmaceutically acceptable chemical derivative thereof to a mammalian patient in need of such treatment.

DETAILED DESCRIPTION OF THE PREFERRED EMBODIMENT

Naloxone hydrochloride is commercially available from Endo Laboratories, Inc., a subsidiary of the DuPont Company, 1000 Stewart Avenue, Garden City, N.Y. 11530. The preparation of naloxone is disclosed in U.S. Pat. No. 3,254,088.

The term pharmaceutically acceptable salts, as used herein, refers to the physiologically acceptable acid addition salts of naloxone such as the hydrochloride, hydrobromide, hydroiodide, acetate, valerate, oleate, etc.

Liquid dosage forms for topical administration includes acceptable emulsions, solutions and suspensions containing volatile diluents commonly used in the art, such as alcohol, glycol and the like. Besides such diluents, topically applied compositions may also include wetting agents, emulsifying and suspending agents.

In the practice of this invention naloxone in the form of a pharmaceutically acceptable salt such as the hydrochloride and pharmaceutically acceptable chemical derivatives thereof such as naltrexone which is the n-methyl cyclopropyl derivative are incororated into solutions, lotions, creams, and ointments for topical application in concentrations of from 0.01 to about 5 percent by weight. These topical products are applied to the skin 1 to 8 times daily. The relief experienced by those receiving the topical application was prompt although temporary.

EXAMPLE 1

1 percent by weight naloxone hydrochloride was incorporated into a solution composed of 70 percent by volume ethyl alcohol and 30 percent by volume propylene glycol and applied 6 times daily to 2 mosquito bites of less than 24 hours duration on a 11 year-old male. This child noted relief from his itching within 10 minutes of each application and the relief lasted 2-4 hours.

EXAMPLE 2

A 0.05% by weight naloxone hydrochloride was incorporated into Eucerin ® cream and applied 4 times daily to the body of a 60 year-old male with intractable itching due to mycosis fungoides. Eucerin ® cream is a synthetic lanolin containing cream produced by Beiersdorf, Inc. of South Norwalk, Conn. 06854. This was the first topical product the patient used that provided him with any significant relief from his itching.

EXAMPLE 3

An ointment composed chiefly of petrolatum and containing 0.01% by weight naloxone hydrochloride was applied 4 times daily to the body of a 60 year-old male with mycosis fungoides. Itching was diminished, although not as much as with the higher concentration of naloxone in Example 2.

EXAMPLE 4

0.1% by weight naloxone hydrochloride was incorporated into a zinc shake lotion and applied to the mosquitoe bites of a 6 year-old girl during a one month five interval in the summer. This lotion provided excellent relief from the itching.

EXAMPLE 5

5% by weight naloxone hydrochloride was incorporated into an ointment and applied 4 times daily for two days to a small eczematous patch on the left hand of a 38 year-old male. Itching was dramatically reduced by each application of the test ointment.

It will be apparent to those skilled in the art that only the preferred embodiments have been described by way of exemplification and that there are various modifications which fall within the scope of this invention.

I claim:

1. A method for relieving severe itching in patients in need of such treatment, said method comprising topically administering a therapeutically effective amount of naloxone or a pharmaceutically acceptable salt thereof or naltrexone to a patient in need of such treatment.

2. The method of claim 1, wherein said naloxone or pharmaceutically acceptable salt thereof or naltrexone is present in a solution, lotion, cream or ointment in the range of between about .01 percent by weight to about 5 percent by weight.

3. The method of claim 1, wherein said naloxone or a pharmaceutically acceptable salt thereof or naltrexone is administered to a patient in need of such treatment periodically from 1 to 8 times per day.

4. The method of claim 1, wherein said pharmaceutically acceptable salt of naloxone is a physiologically acceptable acid addition salt.

5. The method of claim 1, wherein said pharmaceutically acceptable salt of naloxone is naloxone hydrochloride.

6. A composition of matter comprising a therapeutically effective amount of naloxone or a pharmaceutically acceptable salt thereof or naltrexone in a lotion, cream or ointment suitable for topical use only.

7. The composition of claim 6, wherein naloxone or a pharmaceutically acceptable salt thereof or naltrexone is present in the lotion, cream or ointment in the range of between about 0.01 percent by weight to about 5 percent by weight.

8. The composition of claim 6, wherein the pharmaceutically acceptable salt of naloxone is a physiologically acceptable acid addition salt.

9. The composition of claim 8, wherein said salt is naloxone hydrochloride.

* * * * *